United States Patent
Hsu et al.

(10) Patent No.: US 7,144,485 B2
(45) Date of Patent: Dec. 5, 2006

(54) STRIPS FOR ANALYZING SAMPLES

(75) Inventors: Tien-Tsai Hsu, Hsinchu (TW); Chia-Te Lai, Hsinchu (TW); Hang-Tang Lin, Taipei (TW)

(73) Assignee: HMD Biomedical Inc., Hsin Chu (TW)

( * ) Notice: Subject to any disclaimer, the term of this patent is extended or adjusted under 35 U.S.C. 154(b) by 430 days.

(21) Appl. No.: 10/341,713

(22) Filed: Jan. 13, 2003

(65) Prior Publication Data

US 2004/0134779 A1    Jul. 15, 2004

(51) Int. Cl.
*G01N 27/327* (2006.01)
*G01N 27/333* (2006.01)

(52) U.S. Cl. .................. 204/403.02; 204/400; 204/416
(58) Field of Classification Search ..............................
204/403.4–403.14, 416–418, 411, 412, 400
See application file for complete search history.

(56) References Cited

U.S. PATENT DOCUMENTS

| | | | |
|---|---|---|---|
| 4,545,382 A | 10/1985 | Higgins et al. | 128/635 |
| 4,711,245 A | 12/1987 | Higgins et al. | 128/635 |
| 5,120,420 A | 6/1992 | Nankai et al. | 204/403 |
| 5,264,103 A | 11/1993 | Yoshioka et al. | 204/403 |
| 5,282,950 A | 2/1994 | Dietze et al. | 204/406 |
| 5,320,732 A | 6/1994 | Nankai et al. | 204/403 |
| 5,437,999 A | 8/1995 | Diebold et al. | 235/288 |
| 5,509,410 A | 4/1996 | Hill et al. | 128/637 |
| 5,628,890 A | 5/1997 | Carter et al. | 204/403 |
| 5,650,062 A * | 7/1997 | Ikeda et al. | 205/778 |
| 5,682,884 A | 11/1997 | Hill et al. | 128/637 |
| 5,727,548 A | 3/1998 | Hill et al. | 128/637 |
| 5,759,364 A | 6/1998 | Charlton et al. | 204/403 |
| 5,820,551 A | 10/1998 | Hill et al. | 600/347 |
| 6,120,676 A | 9/2000 | Heller et al. | 205/777.5 |
| 6,129,823 A | 10/2000 | Hughes et al. | 204/409 |
| 6,143,164 A | 11/2000 | Heller et al. | 205/777.5 |
| 6,241,862 B1 | 6/2001 | McAleer et al. | 204/403 |
| 6,258,229 B1 | 7/2001 | Winarta et al. | 204/403 |
| 6,270,637 B1 | 8/2001 | Crismore et al. | 204/403 |
| 6,299,757 B1 | 10/2001 | Feldman et al. | 205/775 |
| 6,413,410 B1 | 7/2002 | Hodges et al. | 205/775 |
| 6,447,657 B1 | 9/2002 | Bhullar et al. | 204/409 |
| 6,454,921 B1 * | 9/2002 | Hodges et al. | 204/401 |
| 6,461,496 B1 | 10/2002 | Feldman et al. | 205/777.5 |

(Continued)

FOREIGN PATENT DOCUMENTS

EP    0 537 761 A2    4/1993

(Continued)

OTHER PUBLICATIONS

JPO English language translation of Ikeda et al. (JP 11-352093 A).*

*Primary Examiner*—Alex Noguerola
(74) *Attorney, Agent, or Firm*—Fish & Richardson P.C.

(57) ABSTRACT

This invention relates to a strip for analyzing a sample. The strip includes two insulating layers, a spacer layer, and a conducting circuit. The spacer layer is disposed between the two insulating layers, and configured to define, together with the two insulating layers, an adsorption port, a sample chamber, a capillary for delivering a sample from the adsorption port to the sample chamber through the capillary, and a vent for facilitating delivery of the sample into the sample chamber. The conducting circuit, also disposed between the two insulating layers, includes a working electrode, a counter electrode, conducting wires, and connectors. A test agent, reactive to an analyte in a sample, is in association with the electrodes.

15 Claims, 4 Drawing Sheets

U.S. PATENT DOCUMENTS

| | | | |
|---|---|---|---|
| 6,541,216 B1 | 4/2003 | Wilsey et al. | 435/26 |
| 2002/0157947 A1 | 10/2002 | Rappin et al. | 204/403.01 |
| 2004/0224369 A1* | 11/2004 | Cai et al. | 435/7.7 |

FOREIGN PATENT DOCUMENTS

| | | |
|---|---|---|
| EP | 0 685 737 A1 | 12/1995 |
| EP | 1 260 589 A2 | 11/2002 |
| JP | 11-352093 A * | 12/1999 |
| WO | WO 99/08106 | 2/1999 |

* cited by examiner

STRIPS FOR ANALYZING SAMPLES

BACKGROUND

A strip containing an electrochemical biosensor is useful to determine the presence and concentration of an analyte in a sample. Such a strip can be utilized, for example, to monitor glucose levels in diabetic patients.

SUMMARY

This invention features a strip for analyzing a sample, e.g., blood or urine. The strip includes two insulating layers, a spacer layer, and a conducting circuit.

The spacer layer is disposed between the two insulating layers, and configured to define, together with the two insulating layers, an adsorption port, a sample chamber, a capillary for delivering a sample from the adsorption port to the sample chamber through the capillary, and a vent for facilitating delivery of the sample into the sample chamber. An adsorption port is an inlet at an edge of the strip that tapers into a capillary. The spacer layer can further define, together with the two insulating layers, one or more additional adsorption ports, sample chambers, and capillaries.

The conducting circuit is also disposed between the two insulating layers. It includes a working electrode, a counter electrode, conducting wires, and connectors. The conducting circuit can be printed on one or both insulating layers. For example, either all elements of the circuit are printed on one layer or some elements are printed on one layer and the others on the other layer. Both the working electrode and the counter electrode are in association with a test agent reactive to an analyte and at least a portion of each is placed in the sample chamber. The working electrode and the counter electrode are respectively connected to two of the connectors through the conducting wires. The connectors are adapted for electrical connection to a meter capable of measuring an electrical parameter. The test agent is an electron transfer reagent that transports electrons from the analyte to the working electrode. As a result, an analyte-responsive signal is generated and transmitted to the meter when a sample containing the analyte enters the sample chamber and contacts both the working electrode and the counter electrode.

A strip of this invention can also include one or more other features. For example, only one of the two insulating layers has an indentation at the adsorption port so that the adsorption port is defined by the indentation, the other insulating layer, and the spacer layer. Further, the sample chamber, but not the capillary, can be filled with a hydrophilic material. Also, one or more working and counter electrodes can be included in the strip. For example, the strip can include an additional working electrode, a portion of which is disposed in the capillary, to measure the conductivity of the sample in the capillary before it contacts a hydrophilic material, if any, in the sample chamber.

In one embodiment, the strip is a rectangle and has connectors at the rear edge. It can have an adsorption port disposed at the front edge or at one of the two side edges, or two adsorption ports disposed respectively at both side edges, or three adsorption ports respectively disposed respectively at the front edge and at both side edges.

In another embodiment, the strip is a pentagon in the shape of a rectangle having a clipped angle at the front edge, has an adsorption port disposed at the slanting edge corresponding to the clipped angle, and has connectors at the rear edge. Optionally, it includes a second adsorption port disposed at a side edge.

In still another embodiment, the strip is a hexagon in the shape of a rectangle having two clipped angles at the front edge, has two adsorption ports respectively disposed at the two slanting edges corresponding to the two clipped angles, and has connectors at the rear edge.

The strip can further include an indicator electrode, placed at the end of a sample chamber, to indicate that the sample chamber is filled with a sample. To separate the counter electrode from the working and indicator electrodes, the counter electrode can be printed on one insulating layer and the working and the indicator electrodes can be printed on the other insulating layer.

The strip can also include two capillaries bridging two adsorption ports to a sample chamber. It can further include an additional working electrode, two portions of which are placed in the two capillaries, respectively, to indicate the inception and the completion of the filling of the sample chamber with a sample.

The strip can further include two additional working electrodes, an indicator electrode, and a second sample chamber. A sample is delivered to the two sample chambers via the same capillary. At least a portion of the second working electrode is placed in the capillary to measure the conductivity of the sample. At least a portion of the third working electrode, in association with another test agent, is placed in the second sample chamber to measure the concentration of a second analyte in the sample. A portion of the indicator electrode is placed in the capillary to indicator the inception of the filling of the sample chamber. Two other portions of the indicator electrode are placed at the respective ends of the two sample chambers to indicate that the sample chambers are filled with the sample.

The details of one or more embodiments of the invention are set forth in the accompanying drawings and the description below. Other features, objects, and advantages of the invention will be apparent from the description and drawings, and from the claims.

DESCRIPTION OF DRAWINGS

In the drawings, which are not to scale.

Like reference symbols in the various drawings indicate like elements.

DETAILED DESCRIPTION

Four different embodiments of a strip of this invention are shown in FIGS. 1, 2, 3, and 4. The four embodiments are to be construed as merely illustrative, and not limitative of the remainder of the disclosure in any way whatsoever. Without further elaboration, it is believed that one skilled in the art can, based on the description herein, utilize the present invention to its fullest extent.

Figure 1:
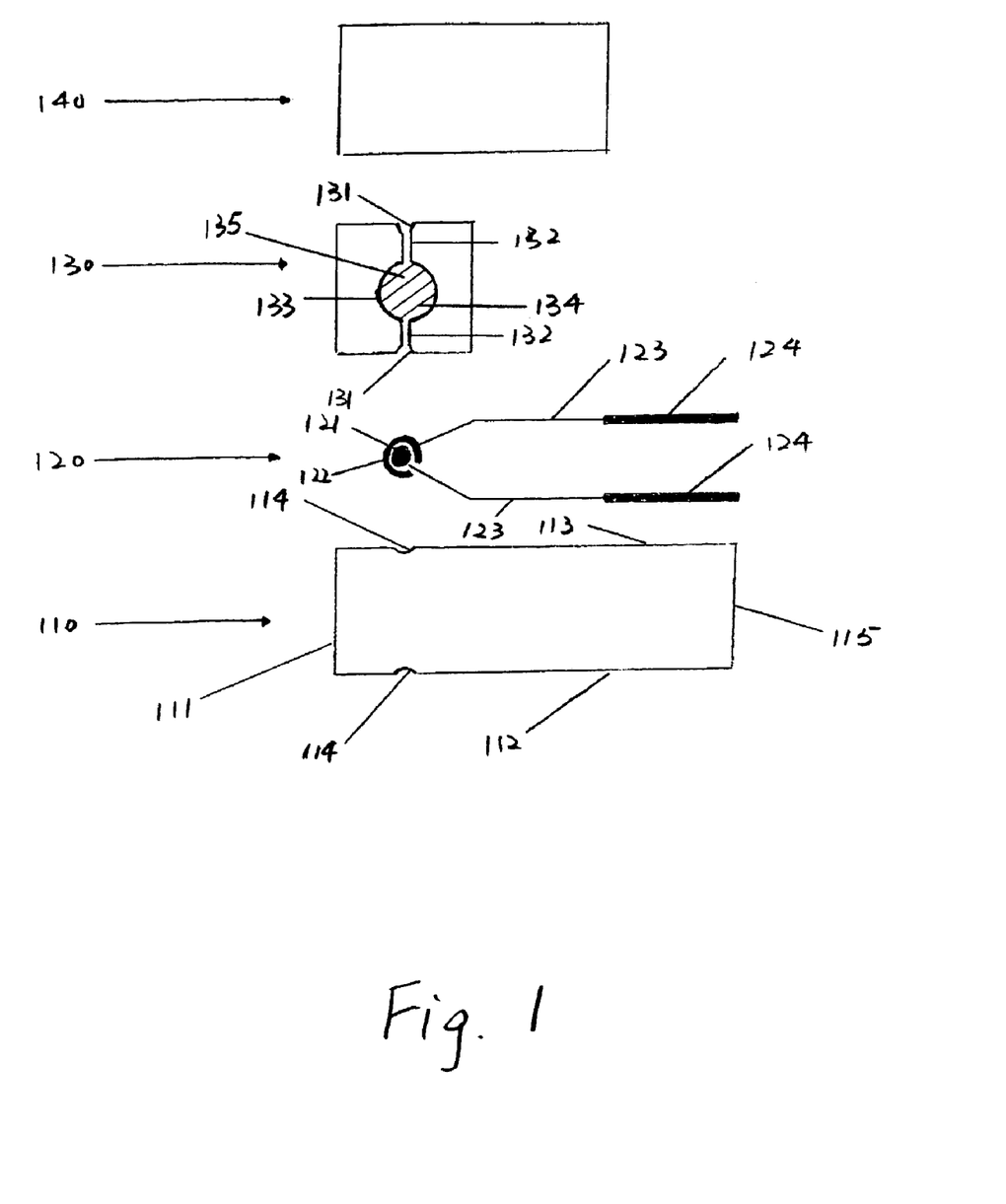
FIG. 1 is an exploded view of a first embodiment of a strip of this invention with a pair of working and counter electrodes, all of which are printed on the same insulating layer.

The strip illustrated in FIG. 1 is a rectangle and includes insulating layer 10 and insulating layer 140. Both insulating layers can be made of any suitable insulating material such as a non-conducting polymer (e.g., polycarbonate, polyolefin, or polyester), or an inorganic material (e.g., metal oxide). Insulating layer 110 further includes front edge 111, side edge 112, side edge 113, rear edge 115 (also the rear edge of the strip), and indentations 114.

Conducting circuit 120, shown in FIG. 1, is printed on insulating layer 110. It includes working electrode 121, counter electrode 122, conducting wires 123, and connectors 124. The term "working electrode" refers to an electrode on which an analyte is electrooxidized or electroreduced in the presence or absence of an electron transfer agent. The term "counter electrode" refers to an electrode paired with a working electrode, through which passes an electrochemical current equal in magnitude and opposite in sign to the current passed through the working electrode. An electrode can be made of an electrically conducting material, such as palladium, platinum, gold, silver, silver/silver chloride, and carbon. Both working electrode 121 and counter electrode 122 respectively connect to two connectors 124 through conducting wires 123. Connectors 124 are disposed at rear edge 115 and adapted for electrical connection to a meter (not shown) capable of measuring one or more electrical parameters, such as current and voltage. The parameters can be detected by amperometry and potentiometry, respectively. Details of these detecting methods can be found, for example, in U.S. Pat. No. 6,299,757, which is incorporated by reference in its entirety.

Overlaying working electrode 121 and counter electrode 122 is spacer layer 130, which is disposed between insulating layer 110 and insulating layer 140. To facilitate connection of connectors 124 to a meter, insulating layer 140 is of such length that it does not cover connectors 124. The spacer layer is typically constructed from a non-conductive adhesive material, such as a pressure-sensitive adhesive or a double-sided adhesive tape. Spacer layer 130, together with insulating layer 110 and insulating layer 140, defines two adsorption ports 131, one sample chamber 133, and two capillaries 132 for delivering a sample from one of the adsorption ports 131 to sample chamber 133 through the corresponding capillary 132. More specifically, either adsorption port 131 is defined by indentation 114, insulating layer 140, and spacer layer 130. The surface on insulating layer 140 facing indentation 114 provides a physical baffle to a sample and facilitates delivery of the sample to capillary 132. Without adsorption port 131, mass-produced strips do not reproducibly draw a sample into capillary 132. When one of the adsorption ports 131 is used to draw a sample, the other adsorption port 131 functions as a vent to facilitate delivery of the sample into sample chamber 133. The two adsorption ports 131 are disposed at side edge 112 and side edge 113, respectively. Sample chamber 133 exposes working electrode 121 and counter electrode 122, both of which are in association with test agent 135. Details of the methods for providing a test agent in an electrochemical biosensor strip can be found, for example, in U.S. Pat. No. 6,299,757.

Whenever practical, a test agent can be provided in a sample. Unlike capillary 132, which is vacant, sample chamber 133 contains a hydrophilic material 134. The term "hydrophilic material" refers to a material (in the form of sheet, film, mesh, or granules) that wicks, filters, and retains a fluid sample and does not prevent diffusion of the sample to the electrodes. The hydrophilic material not only facilitates the uptake of a sample and retains it, but also reduces the required sample volume. Suitable hydrophilic materials include nylon, cellulose, polyvinyl alcohol, and polyvinylpyrolidone. Hydrophilic material 134 is placed inside sample chamber 133 either before or after test agent 135 has been coated onto working electrode 121 and counter electrode 122. Hydrophilic material 134 and test agent 135 can also be mixed and placed inside sample chamber 133, resulting in a coating on working electrode 121 and counter electrode 122. Test agent 135 is an electron transfer agent that, upon reacting with an analyte, transports electrons between the analyte in a sample and working electrode 121. Such electron transfer can be realized either directly via a one-component test agent, such as ferricynide or ferrocence, or indirectly via a two-component test agent, such as a mixture of ferricynide and glucose oxidase or a mixture of ferrocence and glucose oxidase. Surfactant or plasma treatment of the walls of the adsorption port, the capillary, and the sample chamber can further facilitate the uptake of a sample.

When using a strip shown in FIG. 1, the end containing connectors 124 is first plugged into a meter. A sample flows into sample chamber 133, upon contacting adsorption port 131, and immerses both working electrode 121 and counter electrode 122 to form a circuit. With a potential applied between working electrode 121 and counter electrode 122, an analyte-responsive signal is generated and transmitted to the meter. The signal is collected and the concentration of the analyte is calculated and shown on the meter.

Figure 2:
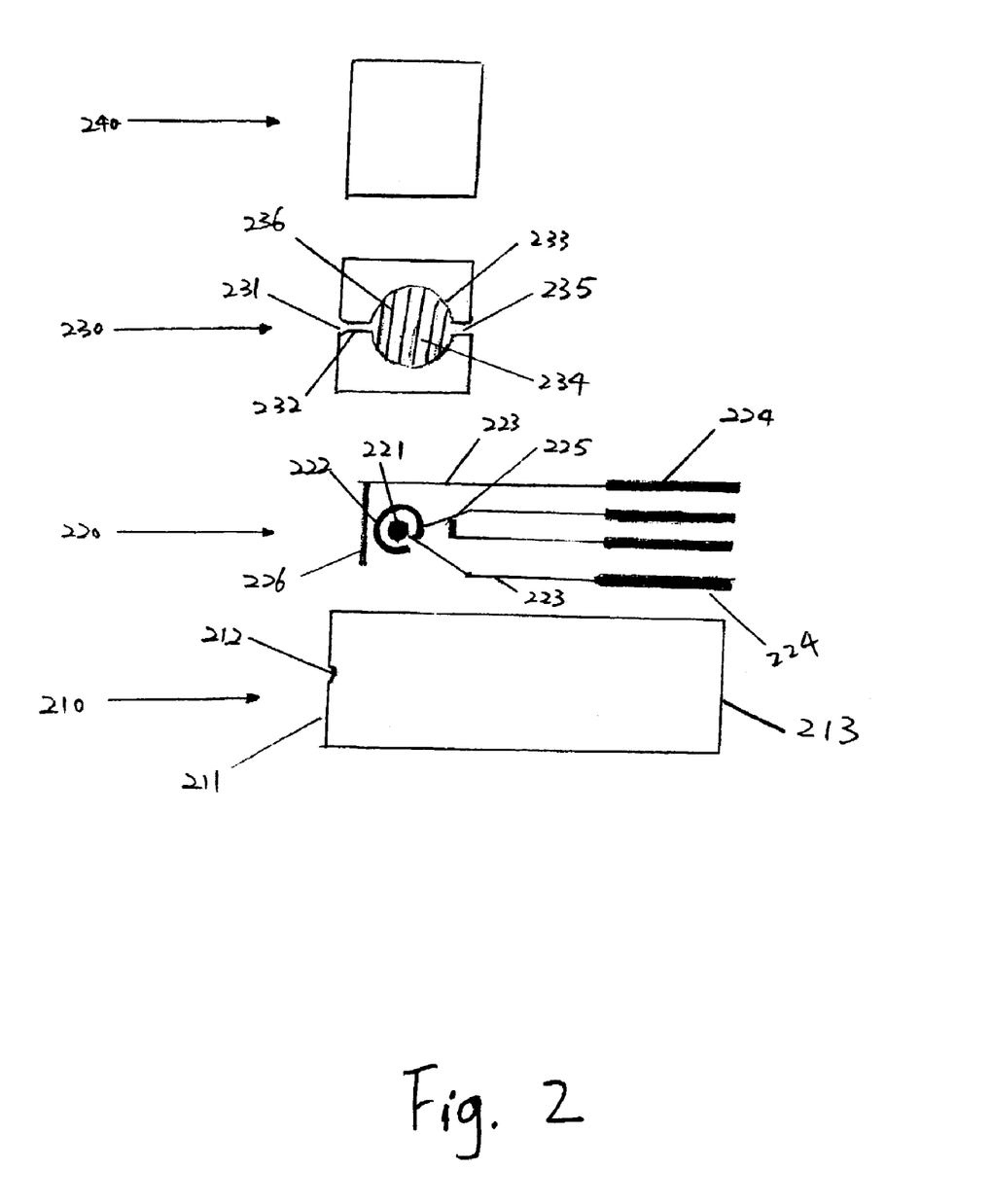
FIG. 2 is an exploded view of a second embodiment of a strip of this invention with two working electrodes, a counter electrode, and an indicator electrode, all of which are printed on the same insulating layer.

FIG. 2 illustrates another embodiment of a rectangular strip of this invention with two working electrodes 221 and 226, an indicator electrode 225, and a counter electrode 222. The term "indicator electrode" refers to an electrode that detects the inception or the completion of the filling of a sample chamber. This strip includes insulating layer 210 and insulating layer 220. Insulating layer 210 further includes front edge 211, rear edge 213, and indentation 212. Similar to that of the strip illustrated in FIG. 1, conducting circuit 220 of this strip is also printed on insulating layer 210. It includes working electrode 221, working electrode 226, counter electrode 222, indicator electrode 225, conducting wires 223, and connectors 224. Conducting wires 223 are coated with a dielectric material (not shown) and connectors 224 are exposed. Unlike the strip shown in FIG. 1, this strip includes indicator electrode 225 and working electrode 226, both of which are respectively connected to two connectors 224 through conducting wires 223.

The strip illustrated in FIG. 2 contains spacer layer 230. Spacer layer 230, together with insulating layer 210 and insulating layer 240, defines adsorption port 231, sample chamber 233, vent 235, and capillary 232 for delivering a sample from adsorption port 231 to sample chamber 233 through capillary 232. Adsorption port 231 is an inlet to capillary 232 and vent 235 is an opening of sample chamber 233 distal to adsorption port 231. Sample chamber 233 exposes working electrode 221 and counter electrode 222, capillary 232 exposes working electrode 226, and vent 235 exposes indicator electrode 225. Hydrophilic material 234 is placed inside sample chamber 233 and test agent 236 is coated on working electrode 221 and counter electrode 222.

When a sample contacts both indicator electrode 225 and counter electrode 222, a circuit is formed and a signal is generated and transmitted to a meter to indicate that the sample chamber is filled with the sample. Another circuit is formed when a sample contacts both working electrode 226 in capillary 232 and counter electrode 222 in sample chamber 233. With a potential applied between working electrode 226 and counter electrode 222, a signal corresponding to the conductivity of the sample is consequently generated and transmitted to a meter. When a sample enters sample chamber 233 and contacts both working electrode 221 and counter electrode 222, still another circuit is formed and a signal corresponding to the concentration of an analyte in the sample is generated and transmitted to the meter with a potential applied to these two electrodes.

Figure 3:
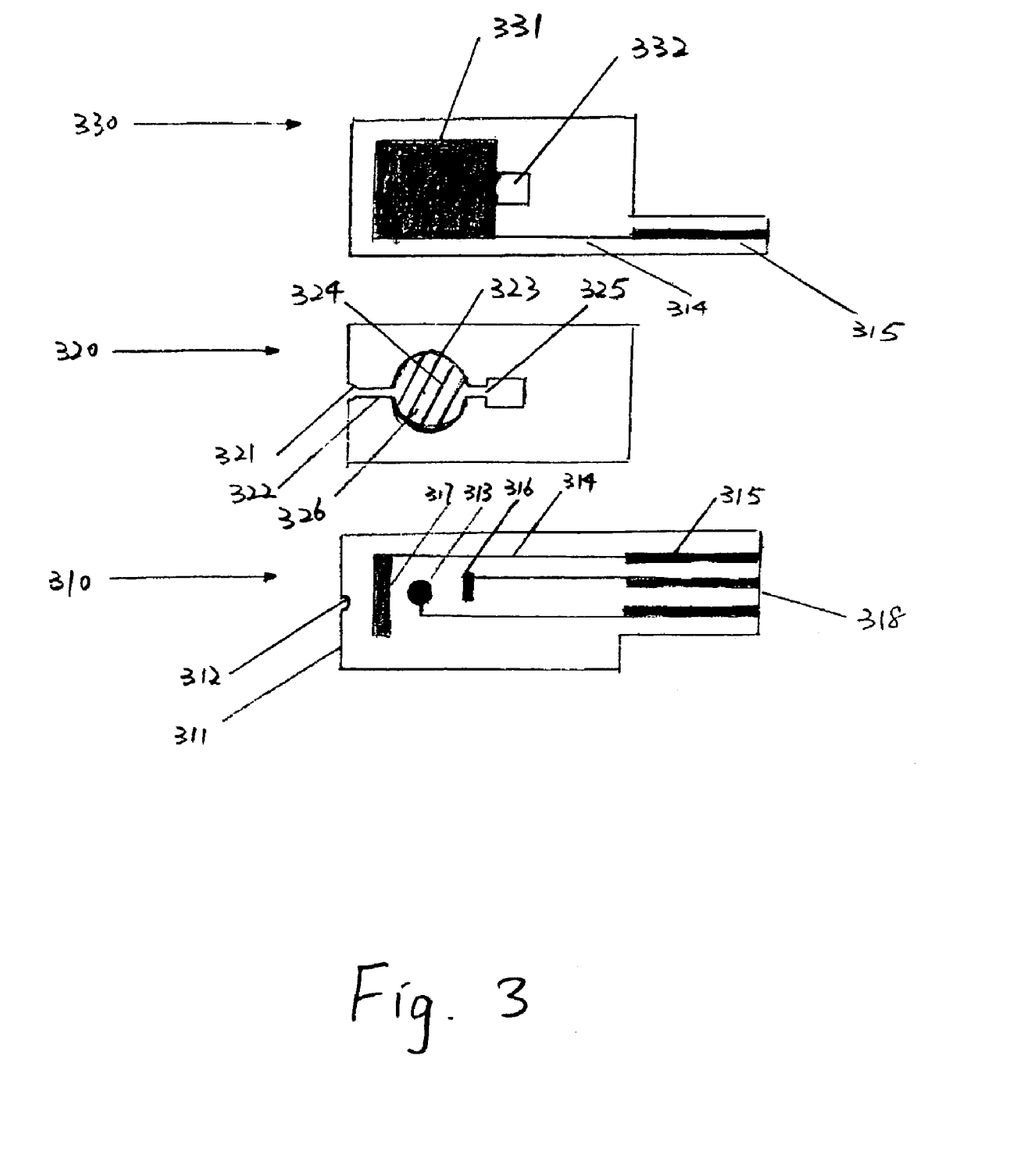
FIG. 3 is an exploded view of a third embodiment of a strip of this invention with two working electrodes and an indicator electrode, which are printed on an insulating layer, and a counter electrode, which is printed on another insulating layer.

FIG. 3 illustrates another embodiment of a rectangular strip of this invention with counter electrode 331 printed on one insulating layer 330, and two working electrodes 313 and 317 and one indicator electrode 316 printed on the other insulating layer 310. This strip includes insulating layer 310, insulating layer 330, and a conducting circuit, which consists of the above-mentioned electrodes, conducting wires 314, and connectors 315. Insulating layer 310 further includes front edge 311, indentation 312, rear edge 318, and hole 332.

Part of the conducting circuit, including working electrode 313, working electrode 317, and indicator electrode 316 and their corresponding conducting wires 314 and connectors 315, is printed on insulating layer 310. The remainder of the conducting circuit, including counter electrode 331, is printed on insulating layer 330. Connectors 315 are exposed at rear edge 318.

Spacer layer 320, together with insulating layer 310 and insulating layer 330, defines adsorption port 321, sample chamber 323, vent 325, and capillary 322 for delivering a sample from adsorption port 321 to sample chamber 323 through capillary 322. Adsorption port 321 is an inlet at front edge 311. Vent 325, an opening of sample chamber 323 distal to adsorption port 321, is in communication with hole 332. Sample chamber 323 exposes working electrode 313 and a portion of counter electrode 331. Capillary 322 exposes working electrode 317 and another portion of counter electrode 331. Vent 325 exposes indicator electrode 316 and another portion of counter electrode 331. Hydrophilic material 324 and test agent 326 are placed inside sample chamber 323. By exposing a portion of counter electrode 331 and a portion of working electrode 317 in capillary 322, the conductivity of a sample can be accurately measured without interference of hydrophilic material 324. Such interference normally occurs when counter electrode 331 is exposed in sample chamber 323, but not in capillary 322.

The strip illustrated in FIG. 3 generates an electrochemical signal in a manner similar to that illustrated in FIG. 2. When a sample containing an analyte contacts counter electrode 331 as well as working electrode 313, working electrode 317, and indicator electrode 316, three circuits are formed and signals are generated and transmitted to a meter showing the concentration of the analyte, the conductivity of the sample, and the completion of the filling of sample chamber 323 with the sample, respectively.

Figure 4:
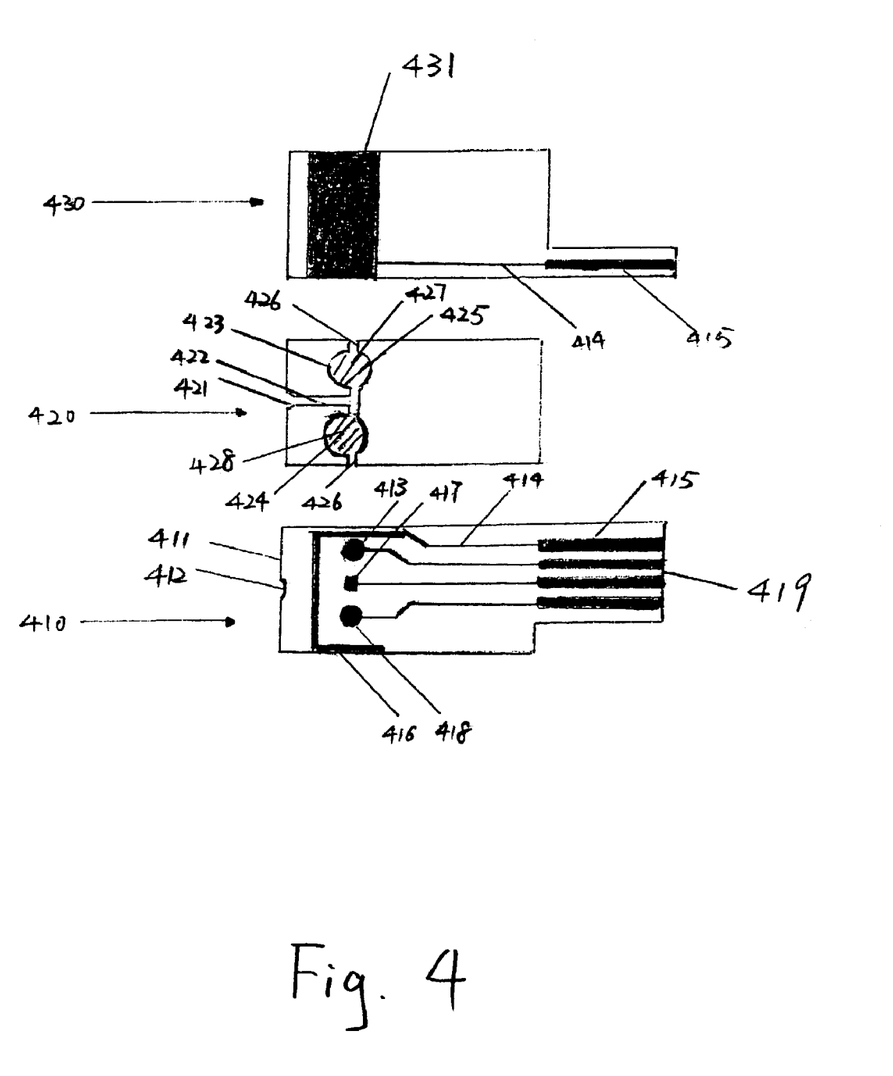
FIG. 4 is an exploded view of a fourth embodiment of a strip of this invention having two sample chambers. This strip includes three working electrodes and an indicator electrode, which are printed on a first insulating layer, and a counter electrode, which is printed on a second insulating layer.

Still another embodiment of a rectangular strip of this invention is illustrated in FIG. 4. It includes insulating layer 410, insulating layer 430, and a conducting circuit, which consists of the above-mentioned electrodes, conducting wires 414, and connectors 415. Insulating layer 410 further includes front edge 411, rear edge 419, and indentation 412.

Part of the conducting circuit, including working electrode 413, working electrode 417, working electrode 418, and indicator electrode 416, and the corresponding conducting wires 414 and connectors 415, is printed on insulating layer 410. The remainder of the conducting circuit, including counter electrode 431, is printed on insulating layer 430. Connectors 415, disposed at rear edge 419, are exposed.

Spacer layer 420, together with insulating layer 410 and insulating layer 430, defines adsorption port 421, sample chamber 423, sample chamber 424, two vents 426, and capillary 422 for delivering a sample from adsorption port 421 to sample chamber 423 and sample chamber 424 through capillary 422. Adsorption port 421 is disposed at front edge 411. Vents 426 are, respectively, openings of sample chamber 423 and sample chamber 424, both distal to adsorption port 421. Sample chamber 423 exposes working electrode 413 and a portion of counter electrode 431. Sample chamber 424 exposes working electrode 418 and another portion of counter electrode 431. Capillary 422 exposes working electrode 417 and a third portion of counter electrode 431. A portion of indicator electrode 416 is positioned in capillary 422 in front of working electrode 417. Two other portions of indicator electrode 416 are positioned, respectively, at an end of sample chamber 423 distal to adsorption port 421 and an end of sample chamber 424 distal to adsorption port 421. Sample chamber 423 and sample chamber 424 both contain hydrophilic material 425. Test agent 427 and test agent 428, reagents reactive to two different analytes in a sample, are placed respectively inside sample chamber 423 and sample chamber 424.

When a sample containing two analytes enters capillary 422 and contacts both a portion of counter electrode 431 and a portion of the indicator electrode 416, a circuit is formed and a signal is generated and transmitted to a meter to indicate the inception of the filling of the sample. When the sample moves forward and contacts working electrode 417, a potential being applied between working electrode 417 and counter electrode 431, another signal is generated and transmitted to the meter to measure the conductivity of the sample. Two other circuits are formed when the sample contacts working electrode 413 and a portion of counter electrode 431 in sample chamber 423, and contacts working electrode 418 and a portion of counter electrode 431 in sample chamber 424, respectively. With a potential applied between working electrode 413 and counter electrode 431, an analyte-responsive signal is generated and transmitted to the meter to measure the concentration of the first analyte in the sample. Similarly, with a potential applied between working electrode 418 and counter electrode 431, another analyte-responsive signal is generated and transmitted to the meter to measure the concentration of the second analyte.

Note that the magnitude of a signal is generally proportional to the surface area of an electrode in contact with a sample. The contacting surface area of indicator electrode 416 increases by two folds when the sample reaches the two portions of indicator electrode 416 at the two vents 426 of sample chamber 423 and sample chamber 424. As a result, the magnitude of the signal passing through indicator electrode 416 also increases by two folds, indicating that sample chamber 423 and sample chamber 424 are filled with the sample.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A strip for analyzing a sample comprising:
   a first insulating layer;
   a second insulating layer;
   a spacer layer disposed between the first and second insulating layers, and configured to define, together with the first and second insulating layers, an adsorption port, a sample chamber, and a capillary for delivering a sample from the adsorption port to the sample chamber; wherein the adsorption port is outwardly enlarged from the capillary and only one of the first and second insulating layers has an indentation at the adsorption port, which is defined by the indentation, the other insulating layer, and the spacer layer; and
   a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter;
   wherein the sample chamber is filled with a hydrophilic material, the strip is a rectangle and has a side edge and a rear edge, the adsorption port being disposed at the side edge, and the connectors being disposed at the rear edge;
   whereby an analyte-responsive signal is generated and transmitted to the meter when a sample containing the analyte enters the sample chamber and contacts both the working electrode and the counter electrode.

2. A strip for analyzing a sample comprising:
   a first insulating layer;
   a second insulating layer;
   a spacer layer disposed between the first and second insulating layers, and configured to define, together with the first and second insulating layers, an adsorption port, a sample chamber, and a capillary for delivering a sample from the adsorption port to the sample chamber; wherein the adsorption port is outwardly enlarged from the capillary and only one of the first and second insulating layers has an indentation at the adsorption port, which is defined by the indentation, the other insulating layer, and the spacer layer; and
   a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter;
   wherein the sample chamber is filled with a hydrophilic material, the strip is a pentagon in the shape of a rectangle having a clipped angle and has a front edge and a rear edge, first and second side edges, and a slanting edge, corresponding to the clipped angle, between the front edge and the first side edge; the spacer layer, together with the first and second insulating layers, further defines a second adsorption port and a second capillary for delivering a sample from the second adsorption port to the sample chamber through the second capillary; the connectors are disposed at the rear edge; the first and second adsorption ports are disposed at the second side edge and the slanting edge, respectively; and only one of the first and second insulating layers has a second indentation at the second adsorption port, which is defined by the second indentation, the other insulating layer, and the spacer layer;
   whereby an analyte-responsive signal is generated and transmitted to the meter when a sample containing the analyte enters the sample chamber and contacts both the working electrode and the counter electrode.

3. A strip for analyzing a sample comprising:
   a first insulating layer;
   a second insulating layer;
   a spacer layer disposed between the first and second insulating layers, and configured to define, together with the first and second insulating layers, an adsorption port, a sample chamber, and a capillary for delivering a sample from the adsorption port to the sample chamber; wherein the adsorption port is outwardly enlarged from the capillary and only one of the first and second insulating layers has an indentation at the adsorption port, which is defined by the indentation, the other insulating layer, and the spacer layer; and
   a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter;
   wherein the sample chamber is filled with a hydrophilic material, the strip is a hexagon in the shape of a rectangle having two clipped angles and has a front edge and a rear edge, first and second side edges, and first and second slanting edges, corresponding to the two clipped angles, between the front edge and the first side edge and between the front edge and the second side edge, respectively; the spacer layer, together with the first and second insulating layers, further defines a second adsorption port and a second capillary for delivering a sample from the second adsorption port to the sample chamber through the second capillary; the connectors are disposed at the rear edge; the first and second adsorption ports are disposed at the first and second slanting edges, respectively; and only one of the first and second insulating layers has a second indentation at the second adsorption port, which is defined by the second indentation, the other insulating layer, and the spacer layer;
   whereby an analyte-responsive signal is generated and transmitted to the meter when a sample containing the analyte enters the sample chamber and contacts both the working electrode and the counter electrode.

4. A strip for analyzing a sample comprising:

a first insulating layer;

a second insulating layer;

a spacer layer disposed between the first and second insulating layers, and configured to define, together with the first and second insulating layers, an adsorption port, a sample chamber, and a capillary for delivering a sample from the adsorption port to the sample chamber; wherein the adsorption port is outwardly enlarged from the capillary and only one of the first and second insulating layers has an indentation at the adsorption port, which is defined by the indentation, the other insulating layer, and the spacer layer; and a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter;

wherein the sample chamber is filled with a hydrophilic material, the strip is a rectangle and has first and second side edges and a rear edge; the spacer layer, together with the first and second insulating layers, further defines a second adsorption port and a second capillary for delivering a sample from the second adsorption port to the sample chamber through the second capillary; the first and second adsorption ports are disposed at the first and second side edges, respectively; the connectors are disposed at the rear edge; and only one of the first and second insulating layers has a second indentation at the second adsorption port, which is defined by the second indentation, the other insulating layer, and the spacer layer;

whereby an analyte-responsive signal is generated and transmitted to the meter when a sample containing the analyte enters the sample chamber and contacts both the working electrode and the counter electrode.

5. A strip for analyzing a sample comprising:

a first insulating layer;

a second insulating layer;

a spacer layer disposed between the first and second insulating layers, and configured to define, together with the first and second insulating layers, an adsorption port, a sample chamber, and a capillary for delivering a sample from the adsorption port to the sample chamber; wherein the adsorption port is outwardly enlarged from the capillary and only one of the first and second insulating layers has an indentation at the adsorption port, which is defined by the indentation, the other insulating layer, and the spacer layer; and a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter;

wherein the sample chamber is filled with a hydrophilic material, the strip is a rectangle and has a front edge and a rear edge, and first and second side edges; the spacer layer, together with the first and second insulating layers, further defines second and third adsorption ports, and second and third capillaries for delivering a sample from the second and third adsorption ports to the sample chamber through the second and third capillaries, respectively; the first, second, and third adsorption ports are disposed at the front edge, the first side edge, and the second side edge, respectively; the connectors are disposed at the rear edge; only one of the first and second insulating layers has a second indentation at the second adsorption port, which is defined by the second indentation, the other insulating layer, and the spacer layer; and only one of the first and second insulating layers has a third indentation at the third adsorption port, which is defined by the third indentation, the other insulating layer, and the spacer layer;

whereby an analyte-responsive signal is generated and transmitted to the meter when a sample containing the analyte enters the sample chamber and contacts both the working electrode and the counter electrode.

6. A strip for analyzing a sample comprising:

a first insulating layer;

a second insulating layer;

a spacer layer disposed between the first and second insulating layers, and configured to define, together with the first and second insulating layers, an adsorption port, a sample chamber, and a capillary for delivering a sample from the adsorption port to the sample chamber; wherein the adsorption port is outwardly enlarged from the capillary and only one of the first and second insulating layers has an indentation at the adsorption port, which is defined by the indentation, the other insulating layer, and the spacer layer; and a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter; the conducting circuit further comprising an indicator electrode, disposed between the first and second insulating layers and electrically connected to one of the connectors, to indicate that the sample chamber is filled with a sample when the sample contacts both the indicator electrode and the counter electrode, the indicator electrode being positioned at an end of the sample chamber distal to the adsorption port;

wherein the sample chamber is filled with a hydrophilic material, the strip is a rectangle and has a side edge and a rear edge, the adsorption port is disposed at the side edge, and the connectors are disposed at the rear edge;

whereby an analyte-responsive signal is generated and transmitted to the meter when a sample containing the analyte enters the sample chamber and contacts both the working electrode and the counter electrode.

7. The strip of claim 6, wherein the indicator electrode and the working electrode are printed on the first insulating layer and the counter electrode is printed on the second insulating layer, and the second insulating layer has a hole in communication with the sample chamber to form a vent.

8. A strip for analyzing a sample comprising:
a first insulating layer;
a second insulating layer;
a spacer layer disposed between the first and second insulating layers, and configured to define, together with the first and second insulating layers, an adsorption port, a sample chamber, and a capillary for delivering a sample from the adsorption port to the sample chamber; wherein
the adsorption port is outwardly enlarged from the capillary and only one of the first and second insulating layers has an indentation at the adsorption port, which is defined by the indentation, the other insulating layer, and the spacer layer; and
a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter; the conducting circuit further comprising an indicator electrode, disposed between the first and second insulating layers and electrically connected to one of the connectors, to indicate that the sample chamber is filled with a sample when the sample contacts both the indicator electrode and the counter electrode, the indicator electrode being positioned at an end of the sample chamber distal to the adsorption port;
wherein the sample chamber is filled with a hydrophilic material, the strip is a rectangle and has a front edge and a rear edge, the adsorption port is disposed at the front edge, the connectors are disposed at the rear edge, the indicator electrode and the working electrode are printed on the first insulating layer and the counter electrode is printed on the second insulating layer, and the second insulating layer has a hole in communication with the sample chamber to form a vent;
whereby an analyte-responsive signal is generated and transmitted to the meter when a sample containing the analyte enters the sample chamber and contacts both the working electrode and the counter electrode.

9. A strip for analyzing a sample comprising:
a first insulating layer;
a second insulating layer;
a spacer layer disposed between the first and second insulating layers, and configured to define, together with the first and second insulating layers, an adsorption port, a sample chamber, and a capillary for delivering a sample from the adsorption port to the sample chamber; wherein the adsorption port is outwardly enlarged from the capillary and only one of the first and second insulating layers has an indentation at the adsorption port, which is defined by the indentation, the other insulating layer, and the spacer layer; and
a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter the conducting circuit further comprising a second working electrode, disposed between the first and second insulating layers and electrically connected to one of the connectors, to measure the conductivity of a sample when the sample contacts both the second working electrode and the counter electrode, at least a portion of the second working electrode being placed in the capillary;
wherein the sample chamber is filled with a hydrophilic material, the strip is a rectangle and has a rear edge and first and second side edges; the spacer layer, together with the first and second insulating layers, further defines a second adsorption port and a second capillary for delivering a sample from the second adsorption port to the sample chamber through the second capillary; a second portion of the second working electrode is disposed at the second capillary distal to the first adsorption port so that the second working electrode first indicates that a sample enters the first capillary when the sample contacts both the first portion of the second working electrode in the first capillary and the counter electrode, and then indicates that the sample chamber is filled with the sample when the sample contacts both the second portion of the second working electrode in the second capillary and the counter electrode; the first and second adsorption ports are disposed at the first and second side edges, respectively; the connectors are
disposed at the, rear edge; and only one of the first and second insulating layers has a second
indentation at the second adsorption port, which is defined by the second indentation, the other insulating layer, and the spacer layer;
whereby an analyte-responsive signal is generated and transmitted to the meter when a sample, containing the analyte enters the sample chamber and contacts both the working electrode and the counter electrode.

10. A strip for analyzing a sample comprising:
a first insulating layer;
a second insulating layer;
a spacer layer disposed between the first and second insulating layers, and configured to define, together with the first and second insulating layers, an adsorption port, a sample chamber, and a capillary for delivering a sample from the adsorption port to the sample chamber; wherein the adsorption port is outwardly enlarged from the capillary and only one of the first and second insulating layers has an indentation at the adsorption port, which is defined by the indentation, the other insulating layer, and the spacer layer; and
a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter; the conducting circuit further comprising a second working electrode, disposed between the first and second insulating layers and electrically connected to one of the connectors, to measure the conductivity of a sample when the sample contacts both the second working electrode and the counter electrode, at least a portion of the second working electrode being placed in the capillary; the conducting circuit further comprising an indicator electrode, printed on the first insulating layer and electrically connected to one of the connectors, to indicate that the sample chamber is filled with a sample when the sample contacts both the indicator electrode and the counter electrode, the indicator electrode being positioned at an end of the sample chamber distal to the adsorption port;

wherein the sample chamber is filled with a hydrophilic material, the strip is a rectangle and has a front edge and a rear edge; the adsorption port is disposed at the front edge; the connectors are disposed at the rear edge; the first and second working electrodes are printed on the first insulating layer and the counter electrode is printed on the second insulating layer; and the second insulating layer has a hole in communication with the sample chamber to form a vent;

whereby an analyte-responsive signal is generated and transmitted to the meter when a sample containing the analyte enters the sample chamber and contacts both the working electrode and the counter electrode.

11. A strip for analyzing a sample comprising:

a first insulating layer;

a second insulating layer;

a spacer layer disposed between the first and second insulating layers, and configured to define, together with the first and second insulating layers, an adsorption port, a sample chamber, and a capillary for delivering a sample from the adsorption port to the sample chamber; wherein the adsorption port is outwardly enlarged from the capillary and only one of the first and second insulating layers has an indentation at the adsorption port, which is defined by the indentation, the other insulating layer, and the spacer layer; and a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter; the conducting circuit further comprising a second working electrode, disposed between the first and second insulating layers and electrically connected to one of the connectors, to measure the conductivity of a sample when the sample contacts both the second working electrode and the counter electrode, at least a portion of the second working electrode being placed in the capillary; the conducting circuit further comprising an indicator electrode, printed on the first insulating layer and electrically connected to one of the connectors, to indicate that the sample chamber is filled with a sample when the sample contacts both the indicator electrode and the counter electrode, the indicator electrode being positioned at an end of the sample chamber distal to the adsorption port;

wherein the sample chamber is filled with a hydrophilic material, the strip is a rectangle and has a side edge and a rear edge; the adsorption port is disposed at the side edge; the connectors are disposed at the rear edge; the working electrode is printed on the first insulating layer and the counter electrode is printed on the second insulating layer; and the second insulating layer has a hole in communication with the sample chamber to form a vent;

whereby an analyte-responsive signal is generated and transmitted to the meter when a sample containing the analyte enters the sample chamber and contacts both the working electrode and the counter electrode.

12. A strip for analyzing a sample comprising:

a first insulating layer;

a second insulating layer;

a spacer layer disposed between the first and second insulating layers, and configured to define, together with the first and second insulating layers, an adsorption port, a sample chamber, and a capillary for delivering a sample from the adsorption port to the sample chamber; wherein the adsorption port is outwardly enlarged from the capillary and only one of the first and second insulating layers has an indentation at the adsorption port, which is defined by the indentation, the other insulating layer, and the spacer layer; and a conducting circuit also disposed between the first and second insulating layers; the conducting circuit having a working electrode, a counter electrode and connectors; at least a portion of the working electrode and the counter electrode being in association with a test agent reactive to an analyte and placed in the sample chamber; the connector being electrically connected to the working electrode and the counter electrode, and being adapted for electrical connection to a meter capable of measuring an electrical parameter; the conducting circuit further comprising a second working electrode, disposed between the first and second insulating layers and electrically connected to one of the connectors, to measure the conductivity of a sample when the sample contacts both the second working electrode and the counter electrode, at least a portion of the second working electrode being placed in the capillary; the conducting circuit further comprising an indicator electrode and a third working electrode, both printed on the first insulating layer and electrically connected to two of the connectors, respectively;

wherein the sample chamber is filled with a hydrophilic material, the strip is a rectangle and has a front edge and a rear edge and first and second side edges; the spacer layer, together with the first and second insulating layers, further defines a second sample chamber so that a sample can be delivered from the adsorption port to the first and second sample chambers through the capillary; the adsorption port is disposed at the front edge; the connectors are disposed at the rear edge; the first and second working electrodes are printed on the first insulating layer; the counter electrode is printed on the second insulating layer and two portions of the counter electrode are placed in the capillary and the second sample chamber, respectively; a first portion of the indicator electrode is placed in the capillary and two other portions of the indicator electrode are placed at an end of the first sample chamber and at an end of the second sample chamber, to first indicate that a sample enters the capillary when the sample contacts the first portion of the indicator electrode and the portion of the counter electrode in the capillary, and then indicate that the first and second sample chambers are filled with the sample when the sample contacts the two other portions of the indicator electrode; and at least a portion of the third working electrode is in association with a second test agent reactive to a second analyte and is placed in the second sample chamber, whereby a second analyte-responsive signal is generated and transmitted to the meter when a sample containing the second analyte enters the second sample chamber and contacts both the third working electrode and the portion of the counter electrode in the second sample chamber;

whereby an analyte-responsive signal is generated and transmitted to the meter when a sample containing the analyte enters the sample chamber and contacts both the working electrode and the counter electrode.

13. A strip for analyzing a sample, comprising:

a first side edge, a second side edge, a front edge, and a rear edge;

a first insulating layer and a second insulting layer;

a spacer layer disposed between the first and second insulating layers, and configured to define, together with the first and second insulating layers, a first adsorption port disposed at the first side edge, a second adsorption port disposed at the second side edge, a sample chamber, a first capillary, and a second capillary, wherein either the first capillary is adapted for delivering a sample from the first adsorption port to the sample chamber or the second capillary is adapted for delivering a sample from the second adsorption port to the sample chamber, only one of the first and second insulating layers has a first indentation at the first adsorption port, which is defined by the first indentation, the other insulating layer, and the spacer layer; and only one of the first and second insulating layers has a second indentation at the second adsorption port, which is defined by the second indentation, the other insulating layer, and the spacer layer; and a conducting circuit also disposed between the first and second insulating layers; the conducting circuit having a working electrode, a counter electrode, and connectors; at least a portion of the working electrode and the counter electrode being in association with a test agent reactive to an analyte and placed in the sample chamber; the connectors being disposed at the rear edge, electrically connected to the working electrode and the counter electrode, and adapted for electrical connection to a meter capable of measuring an electrical parameter;

whereby an analyte-responsive signal is generated and transmitted to the meter when a sample containing the analyte enters the sample chamber and contacts both the working electrode and the counter electrode.

14. The strip of claim 13, wherein the first and second adsorption ports are symmetrically disposed at the first and second side edges.

15. The strip of claim 13, wherein the sample chamber is filled with a hydrophilic material.

* * * * *